(12) United States Patent
Ouyang

(10) Patent No.: US 10,974,024 B1
(45) Date of Patent: Apr. 13, 2021

(54) FLUSHABLE MULTI-LUMEN CATHETER DEVICE AND METHOD OF USE

(71) Applicant: Yannan Ouyang, Memphis, TN (US)

(72) Inventor: Yannan Ouyang, Memphis, TN (US)

( * ) Notice: Subject to any disclaimer, the term of this patent is extended or adjusted under 35 U.S.C. 154(b) by 0 days.

(21) Appl. No.: 16/593,168

(22) Filed: Oct. 4, 2019

(51) Int. Cl.
A61M 25/00 (2006.01)
A61M 39/22 (2006.01)

(52) U.S. Cl.
CPC .... *A61M 25/0029* (2013.01); *A61M 25/0017* (2013.01); *A61M 39/227* (2013.01); *A61M 2025/0019* (2013.01); *A61M 2205/3331* (2013.01); *A61M 2210/12* (2013.01)

(58) Field of Classification Search
CPC .......... A61M 25/0017; A61M 25/0021; A61M 25/0023; A61M 25/0028; A61M 25/0029; A61M 25/003; A61M 2025/0018; A61M 2025/0019; A61M 2025/0025; A61M 2025/0035; A61M 2025/0079
See application file for complete search history.

(56) References Cited

U.S. PATENT DOCUMENTS

| | | | |
|---|---|---|---|
| 4,140,119 A * | 2/1979 | Pollack | A61M 25/0068 604/27 |
| 4,227,533 A | 10/1980 | Godfrey | |
| 4,813,935 A * | 3/1989 | Haber | A61M 25/04 604/103 |
| 5,310,524 A | 5/1994 | Campbell et al. | |
| 5,360,403 A * | 11/1994 | Mische | A61M 25/0075 604/101.02 |
| 5,792,118 A * | 8/1998 | Kurth | A61M 25/0017 604/246 |
| 5,807,331 A * | 9/1998 | den Heijer | A61M 25/0021 604/101.05 |
| 6,045,531 A * | 4/2000 | Davis | A61M 25/10 604/101.05 |
| 6,448,062 B1 | 9/2002 | Huth et al. | |
| 10,441,744 B2 | 10/2019 | Ouyang | |
| 2004/0044307 A1* | 3/2004 | Richardson | A61M 25/0017 604/102.01 |
| 2005/0107738 A1* | 5/2005 | Slater | A61M 25/10 604/96.01 |
| 2005/0215978 A1* | 9/2005 | Ash | A61M 25/00 604/508 |

(Continued)

FOREIGN PATENT DOCUMENTS

EP 1854502 B1 3/2010

*Primary Examiner* — Kami A Bosworth
(74) *Attorney, Agent, or Firm* — Veritay Group IP, PLLC; Susan B. Fentress

(57) ABSTRACT

This invention relates to a multi-lumen flushable catheter device and a kit including this device. The multi-lumen catheter is made of a single lumen catheter in fluid connection with a multi-lumen catheter. The multi-lumen catheter includes a fluid lumen and a backflow connection lumen; wherein the fluid lumen and a backflow connection lumen are in fluid communication; a pressure control lumen made of a proximal port to receive a fluid such as air or a liquid and a distal balloon, the distal balloon is configured to block the single lumen catheter to prevent fluid flow into the single lumen catheter, wherein the pressure control lumen is not in fluid connection with the central lumen of the multi-lumen catheter. This device allows cleaning of in dwelling catheter in situ.

8 Claims, 4 Drawing Sheets

(56) References Cited

U.S. PATENT DOCUMENTS

| | | | | |
|---|---|---|---|---|
| 2009/0270815 A1* | 10/2009 | Stamp | ................... | A61M 39/06 |
| | | | | 604/249 |
| 2014/0163530 A1* | 6/2014 | Frenkel | ............... | A61M 25/003 |
| | | | | 604/540 |
| 2014/0246015 A1* | 9/2014 | Einav | ................ | A61M 16/0486 |
| | | | | 128/202.16 |
| 2014/0257243 A1* | 9/2014 | Pruitt | ....................... | A61L 29/16 |
| | | | | 604/508 |
| 2015/0133864 A1* | 5/2015 | Zachar | .................. | A61M 25/10 |
| | | | | 604/96.01 |
| 2015/0343182 A1* | 12/2015 | Vazales | .................. | A61B 1/122 |
| | | | | 604/267 |

\* cited by examiner

FLUSHABLE MULTI-LUMEN CATHETER DEVICE AND METHOD OF USE

CROSS-REFERENCE TO RELATED APPLICATIONS

NONE

FIELD OF THE INVENTION

This invention relates to a multi-lumen flushable catheter device and a method of use.

BACKGROUND OF THE INVENTION

In currently available techniques, a catheter is one of the most widely used medical devices. For patients needing fluid daily, an easy way is to implant the catheter in a patient's body, and the implanted catheter can be used for fluid of medicine, nutrients, or blood and can also be used to draw test blood. After these usages, the implanted catheter needs to be cleaned to prevent contamination and infection. Currently, heparin, the widely used anticoagulant, is used to clean the catheter, followed by saline flushing. Both the clean heparin and flushing saline are infused into the blood stream after cleaning. The disadvantage of this cleaning method is included but not limited to: (1) a large amount of heparin is infused into body, which increases the bleeding risk for many patients; and (2) the cleaning effect can be compromised because the clean solution is infused into blood stream. Using a flushable catheter with a microfluidic valve has been used to control the cleaning and the followed backflow of washing solution. However, this device requires a high accuracy and precision in production which results in a higher cost, making it undesirable for disposable device application.

SUMMARY OF THE INVENTION

This invention relates to a multi-lumen flushable catheter device and a method of use. The inventive subject matter includes: an implantable medical device including a multi-lumen catheter made of a single lumen catheter in fluid connection with a multi-lumen catheter. The multi-lumen catheter being made of: a fluid lumen and a backflow connection lumen; wherein the fluid lumen and a backflow connection lumen are in fluid communication; an pressure control lumen made of of a proximal port to receive a fluid such as aft or a liquid and a distal balloon, the distal balloon configured to block the single lumen catheter to prevent fluid flow into the single lumen catheter, wherein the pressure control lumen is not in fluid connection with the central lumen of the multi-lumen catheter.

The inventive subject matter further includes a kit made of the same implantable medical device including a multi-lumen catheter and cleaning reagents. The cleaning reagents including an at least one prefilled syringe of heparin and an at least one prefilled syringe of physiological saline solution. The inventive subject matter further includes a method to clean an indwelling catheter including the steps of:
providing a multi-lumen catheter made of:
a single lumen catheter in fluid connection with a multi-lumen catheter comprising of a fluid lumen. wherein the fluid lumen and a backflow connection lumen are in fluid communication; an pressure control lumen made of a proximal port to receive a fluid and a distal balloon, the distal balloon configured to block the single lumen catheter to prevent fluid flow into the single lumen catheter, wherein the pressure control lumen is not in fluid connection with the central lumen of the multi-lumen catheter;
inflating the balloon to block the single lumen catheter to prevent fluid flow;
connecting a syringe with cleaning solution to the fluid lumen;
connecting an empty syringe to the backflow connection lumen to remove the cleaning solution; connecting a syringe with saline to the fluid lumen;
connecting an empty syringe to the backflow connection lumen to remove the saline and deflating the balloon to open the single lumen catheter.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

As used herein, the term "implantable medical device" is used throughout the specification to describe implanted medical devices that contain lumens or central cavities that have an interface with a portion of the subject's body, most commonly involving fluid interactions, such as stents, catheters, etc.

As used herein, the term "catheter" is used throughout the specification to describe a thin tube extruded from medical grade materials serving a broad range of functions. Catheters are medical devices that can be inserted in the body to treat diseases or perform a surgical procedure. By modifying the material or adjusting the way catheters are manufactured, it is possible to tailor catheters for cardiovascular, urological, gastrointestinal, neurovascular, and ophthalmic applications. Catheters can be inserted into a body cavity, duct, or vessel. Functionally, they allow drainage, administration of fluids or gases, access by surgical instruments, and also perform a wide variety of other tasks depending on the type of catheter. The process of inserting a catheter is catheterization. In most uses, a catheter is a thin, flexible tube ("soft" catheter) though catheters are available in varying levels of stiffness depending on the application. A catheter left inside the body, either temporarily or permanently, may be referred to as an indwelling catheter. A permanently inserted catheter may be referred to as a permcath. A range of polymers may be used for the construction of catheters, including, but not limited to, silicone rubber, nitinol, nylon, polyurethane, and polyethylene terephthalate (PETE) latex, and/or thermoplastic elastomers. Silicone may be used as it is considered one of the most common choices because it is inert and unreactive to body fluids and a range of medical fluids with which it might come into contact.

As used herein, the term "central lumen" is used throughout the specification to describe a lumen containing a section of a catheter or other medical device, which is the primary path of delivery of a fluid treatment. As used herein, the term "lumen to subject" is used throughout the specification to describe the section of the medical device which serves to directly deliver the fluid treatment to the subject.

As used herein, the term "digestive enzyme" is used throughout the specification to describe enzymes that break down polymeric macromolecules into their smaller building blocks. Digestive enzymes are classified based on their target substrates: proteases and peptidases split proteins into small peptides and amino acids; lipases split fat into three fatty acids and a glycerol molecule; amylases split carbohydrates such as starch and sugars into simple sugars such as glucose; and nucleases split nucleic acids into nucleotides. Digestive enzymes consider all enzymes that can digest the tissue matrixes and/or cell membrane proteins. One specific example of a digestive enzyme is Trypsin. Another exemplary enzyme is papain.

As used herein, the term "calcium deficient buffer with high ion concentration" is used throughout the specification to describe a buffer in which it is substantially calcium ion free or contains a calcium sequestering agent, such as a chelating agent like EDTA or EGTA.

As used herein, the term "physiological saline" is used throughout the specification to describe a sterile solution of sodium chloride (NaCl, more commonly known as salt) in water.

As used herein, the term "chelating agent" is used throughout the specification to describe a chemical or set of chemicals, which are used to absorb or sequester metal ions. Specific examples of chelating agents include EDTA and EGTA.

As used herein, the term "ethylenediaminetetraacetic acid" or "EDTA" is used throughout the specification to describe a hexadentate ligand and chelating agent with the structure:

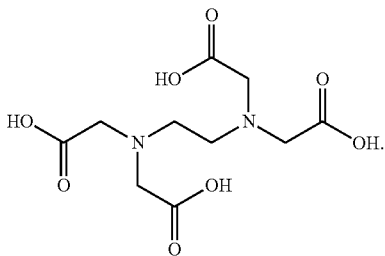 [SMILES: O=C(O)CN(CCN(CC(=O)O)CC(=O)O)CC(=O)O]

As used herein, the term "ethylene glycol tetraacetic acid" or "EGTA" is used throughout the specification to describe a hexadentate ligand and chelating agent with the structure:

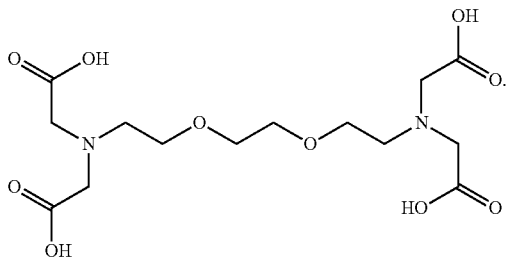 [SMILES: O=C(O)CN(CCOCCOCCN(CC(=O)O)CC(=O)O)CC(=O)O]

As used herein, the term "biofilm" is used throughout the specification to describe any group of microorganisms in which cells stick to each other on a surface. These adherent cells are frequently embedded within a self-produced matrix of extracellular polymeric substance (EPS). Biofilm EPS, which is also referred to as slime (although not everything described as slime is a biofilm), is a polymeric conglomeration generally composed of extracellular DNA, proteins, and polysaccharides. Biofilms may form on living or non-living surfaces and can be prevalent in natural, industrial and hospital settings.

As used herein, the term "bloodstream infections" or "bacteremia" is used throughout the specification to describe presence of bacteria in the blood and the possible resulting infection. The blood is normally a sterile environment, so the detection of bacteria in the blood (most commonly accomplished by blood cultures) is always abnormal. Bacteria can enter the bloodstream as a severe complication of infections (like pneumonia or meningitis), during surgery (especially when involving mucous membranes such as the gastrointestinal tract), or due to catheters and other foreign bodies entering the arteries or veins (including intravenous drug abuse).

As used herein, the term "prevention" or "preventing" is used throughout the specification to describe: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The present invention contemplates the above-described compositions in "therapeutically effective amounts" or "pharmaceutically effective amounts", which means that amount which, when administered to a subject or patient for treating a disease, is sufficient to affect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein, the term "subject" is used throughout the specification to describe any mammal, preferably a human patient, livestock, or domestic pet.

In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

DESCRIPTION OF THE INVENTION

One way to minimize blood contact with the lumen of potentially contaminated catheters is to add a flushing lumen that is connected to the central catheter lumen via a balloon seal. The seal opens the connection between the flushing lumen and the central lumen while blocking access to the bloodstream. As such almost all of the catheter lumen can be filled with a solution to clean and kill bacteria without the risk of introducing the cleaning agents directly into the blood stream. This device makes flushing and disinfecting catheters safer and may also extend the useful life of the inserted catheters. In principle, the application of the balloon seal is safe, reliable and relatively low cost. When the catheters need to be cleaned or washed, the solution can be injected into the wash/flushing lumen. Pressure will inflate the balloon to cut off the connection to the blood stream and open the lumen in the catheter to wash solution. The used wash solution can be released from the central lumen when the balloon is disengaged.

Figure 1:
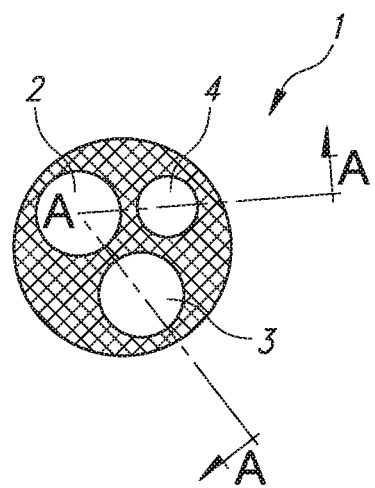
FIG. 1 is an enlarged cross-section showing the device.
Figure 2A:
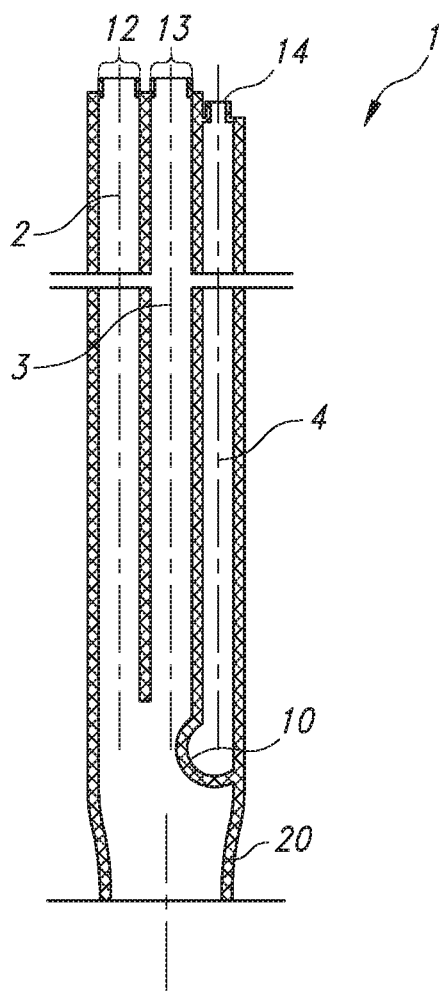
FIG. 2A is a cutaway view of FIG. 1 A-A flattened out.
Figure 2B:
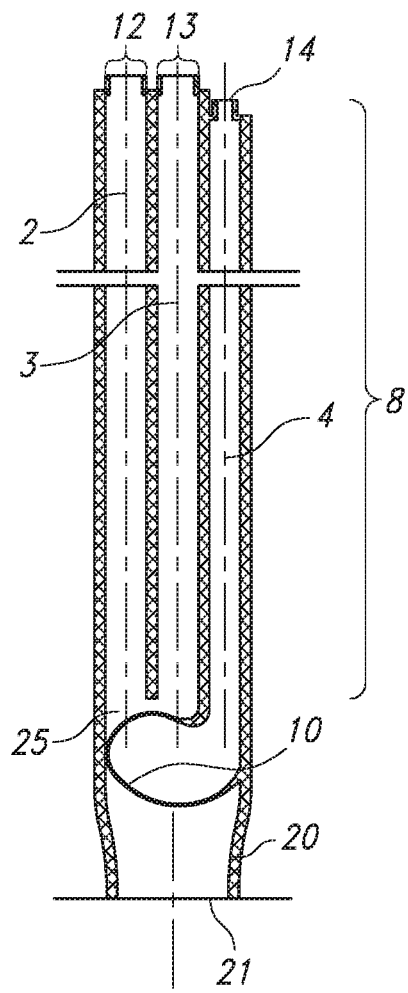
FIG. 2B is a cutaway view of FIG. 1A-A showing the process of cleaning with the present device.
Figure 3A:
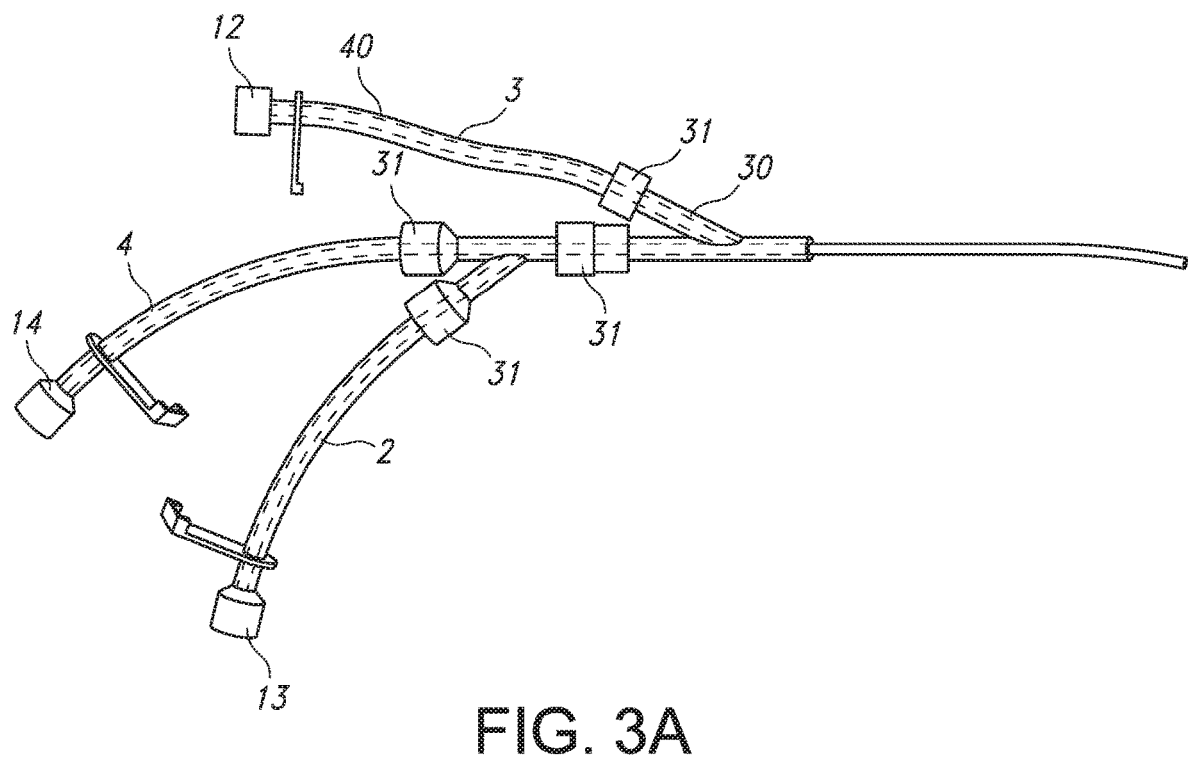
FIG. 3A shows the multi-lumen flushable catheter with the balloon inflation lumen portion of the device open.
Figure 3B:
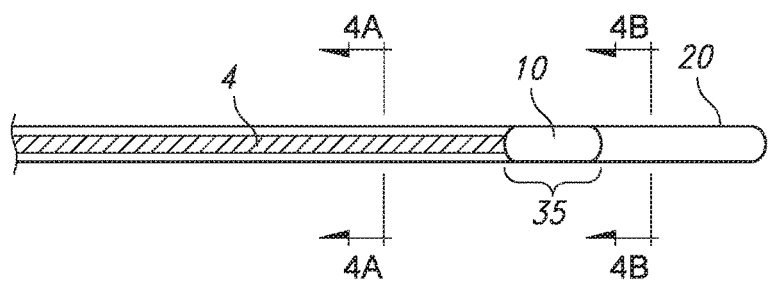
FIG. 3B shows the multi-lumen flushable catheter with the balloon inflation lumen portion of the device closed.

Now referring to FIGS. 1, 2A, 2B, a flushable medical catheter 1 includes a multi-lumen section 8 made of a: fluid lumen 2, a backflow connection lumen 3, and a pressure control lumen 4. In an exemplary embodiment, the fluid lumen 2, backflow connection lumen 3 and the pressure control lumen 4 are modeled together and form a unit. The fluid lumen 2 and backflow connection lumen 3 are in fluid communication. The pressure control lumen 4 is not in fluid communication with the fluid lumen 2 and the backflow connection lumen 3. The pressure control lumen 4 includes a balloon 10. The balloon 10 when inflated blocks the fluid from entering the central lumen 20, which is a single lumen section and is proximal to the subject. The balloon 10 is positioned to allow a pocket 25 to form in the central lumen 20 where fluid from the fluid lumen 2 can enter and then exit from the backflow connection lumen 3. The balloon 10 is positioned near the tip 21 of the flushable medical catheter 1 to allow for a higher degree of cleaning of an implanted catheter.

A pressure control connecting structure 14 functions as a port to receive pressure. The inflated balloon 10 creates a blocking structure to block the fluid exit, and the flushable medical catheter 1 can be cleaned, and the cleaning and washing solutions can be excluded through the backflow lumen 3. The advantage and benefit of the current embodiment includes but is not limited to simple structure, low cost and easy to use.

The balloon 10 can be made of latex, rubber, urethane, a plastic such as polyimide, polyethylene terephthalate or nylons or any suitable material. However, it is best to select a non-allergenic material. In operation, the solution is infused through fluid lumen 2 or backflow lumen 3. When the fluid lumen 2 is under cleaning after fluid, the pressure is inflated in the inflatable balloon, inducing a blocking structure to choke the central lumen of the catheter 20.

In operation a fluid syringe is connected to an injection cap 12 of the fluid lumen 2 and a solution is slowly injected into the multi-lumen catheter 1. If the user wished to clean the flushable medical catheter 1, a pressure syringe is connected to port 14 and sufficient amount of fluid such as air or a liquid is injected to distend the balloon 10 to block the central lumen 20, then a fluid syringe is connected to an injection cap 12 of the fluid lumen 2 and a cleaning or washing solution is slowly injected into fluid lumen 2 and withdrawn by a syringe connected to port 13 of lumen 3. The cleaning or washing solution flows through the fluid lumen 2 and flows out of catheter through backflow lumen 3. This process may be completed several times including both a cleaning solution and a washing solution such as saline.

Figure 4A:
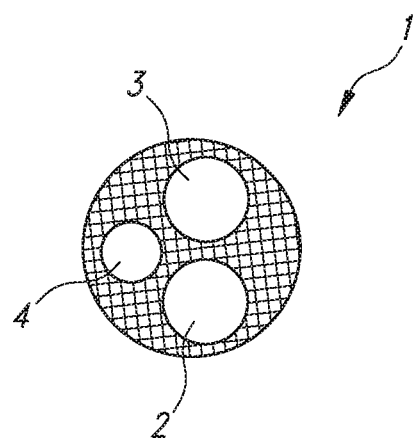
FIG. 4A shows an enlarged cross-section of the multi-lumen portion of the device.
Figure 4B:
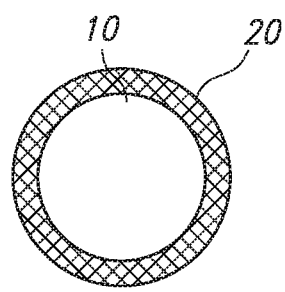
FIG. 4B shows an enlarged cross-section of the single lumen portion of the device.

Now referring to FIGS. 3A-3B & 4A-4B, a catheter 30 is positioned in a subject 50. The catheter 30 terminates in a plurality of luer lock hubs 31. The catheter 30 has a multi-lumen section as shown in FIG. 4A, which terminates in a single lumen section as shown in FIG. 4B. A void 35 in the catheter 30 is positioned between the multi-lumen section and the single lumen section. A balloon 10 is configured to fill void 35 upon receiving a sufficient amount of pressure. A multi-lumen flushing device 40 has a plurality of attachment ports (not shown) to securely connected to each of the plurality of luer lock hubs 31 to form a fluid connection with the catheter 30.

It is an object of this present invention to prevent infusion of cleaning solution into the subject 50. In operation, solution is infused through fluid lumen 2 or backflow lumen 3. When the fluid lumen 2 is under cleaning after fluid, the pressure is inflated in the inflatable balloon 10, inducing a blocking structure to choke the central lumen of the catheter 20. In operation a fluid syringe is connected to an injection cap 12 of the fluid lumen 2 and a solution is slowly injected into the multi-lumen flushing device 40. If the user wished to clean the indwelling catheter 30, an pressure syringe is connected to port 14 and sufficient pressure is injected to distend the balloon 10 to block the central lumen 20 of the catheter 30. Then a fluid syringe is connected to an injection cap 12 of the fluid lumen 2 and a cleaning solution is slowly injected into fluid lumen 2 and withdrawn by a syringe connected to port 13 of lumen 3. The cleaning solution flows through the fluid lumen 2 and flows out of multi-lumen flushing device 40 through the backflow lumen 3. This process may be completed several times including both a cleaning solution and a washing solution such as saline. The pressure syringe can be calibrated to deliver the required unit of pressure in mm Hg based on the size and type of catheter.

In one embodiment, the present invention contemplates a washable catheter affixed to a multi-lumen activated by a balloon seal. In one embodiment, the catheter is designed to prevent bacteria/biofilm contamination without even a minimal introduction of contaminated fluids with bioactive agents into the blood stream of patients. In one embodiment, the catheter is designed to be reused. In one embodiment, a fluidic pressure seal is close to the distal end part of the catheter (lumen to subject) in proximity of the blood vessel. In one embodiment, when activated through the pressure control lumen, the pressure seal closes access to the distal end of the catheter and allows the flow of fluid from the flushing lumen through into the central lumen.

In one embodiment, cleaning reagents may then be used to eliminate any biofilm which may have developed in the catheter central lumen or flushing lumen. In one embodiment, the present invention contemplates a reagent kit designed for use with the catheter with the balloon seal. In one embodiment, a prefilled heparin lock flush syringe is provided. For example, BD POSIFLUSH (BD Biosciences Franklin Lakes, N.J.) Pre-Filled Heparin Lock Flush Syringe is available in two concentrations—10 USP units per mL and 100 USP units per mL to support catheter maintenance practice. In one embodiment, a specific protocol for cleaning that includes exposure to trypsin, a calcium deficient high ion concentration buffer, and 70% ethanol before flushing and normalization with saline solution.

Table 1 presents comparative results of flow rate between the catheter from Bard (the leading producer in the world) and current invention. The infusion rate directly relates to the infusion efficiency. The data in the table shows that the current invention is functionally equivalent to state of art currently available.

TABLE 1

Pressure Injection Flow Rate Testing

| mL/s | Bard (Lumen 1) | Bard (Lumen 2) | Device 1 (Lumen 1) | Device 1 (Lumen 2) |
|---|---|---|---|---|
| 6 | 155 psi | 134 psi | N/A | 124 psi |
| 5 | 119 psi | 101 psi | 191 psi | 92 psi |
| 4 | 87 psi | 71 psi | 79 psi | 43 psi |
| 3 | 46 psi | 42 psi | 51 psi | 32 psi |
| 2 | 27 psi | 22 psi | 32 psi | 23 psi |
| 1 | 11 psi | 8 psi | 24 psi | 12 psi |

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

The invention claimed is:

1. An implantable medical device including a multi-lumen catheter comprising:
a central lumen positioned proximal to a subject, said central lumen comprising a single lumen portion of said multi-lumen catheter, said single lumen portion in fluid connection with a multi-lumen catheter portion comprising a fluid lumen, a backflow connection lumen and a pressure control lumen; wherein the fluid lumen and the backflow connection lumen are in fluid communication within the multi-lumen catheter; and wherein the pressure control lumen is comprised of a proximal port to receive a fluid and a distal balloon, said distal balloon positioned to allow a pocket to form in the central lumen, the distal balloon configured to block the single lumen portion to prevent fluid flow into the single lumen portion, wherein the pressure control lumen is not in fluid connection with the central lumen of the single lumen portion and wherein fluid from the backflow connection lumen can enter the pocket and exit from the fluid lumen if the distal balloon is inflated.

2. The implantable medical device of claim 1, wherein the fluid lumen comprises an injection cap to receive a syringe to infuse a cleaning fluid into the implantable medical device.

3. The implantable medical device of claim 1, wherein the back-flow lumen comprises a port to receive a syringe to withdraw cleaning fluid from the implantable medical device.

4. The implantable medical device of claim 1, wherein said implantable medical device is a central venous catheter.

5. The implantable medical device of claim 1, wherein said implantable medical device is a urinary catheter.

6. A kit comprising:
an implantable medical device comprised of
the central lumen comprising a single lumen portion in fluid connection with a multi-lumen catheter portion comprising a fluid lumen, a backflow connection lumen and a pressure control lumen; wherein the fluid lumen and the backflow connection lumen are in fluid communication within the multi-lumen catheter; and wherein the pressure control lumen is comprised of a proximal port to receive a fluid and a distal balloon, said distal balloon positioned to allow a pocket to form in the central lumen, and wherein the distal balloon is configured to block the single lumen portion to prevent fluid flow into the single lumen portion, wherein the pressure control lumen is not in fluid connection with a central lumen of the single lumen portion wherein fluid from the fluid lumen can enter the pocket and exit from the backflow connection lumen if the distal balloon is inflated;
and cleaning reagents, the cleaning reagents consisting essentially of: at least one prefilled syringe of heparin and at least one prefilled syringe of physiological saline solution.

7. The kit of claim 6 further comprising a fluid syringe.

8. The kit of claim 6 further comprising a pressure syringe calibrated to deliver a sufficient amount of fluid to distend the balloon, wherein the distended balloon blocks the single lumen portion.

* * * * *